United States Patent [19]
Antone

[11] Patent Number: 5,285,022
[45] Date of Patent: Feb. 8, 1994

[54] PARTIAL WEIGHT BEARING SCALE
[76] Inventor: Howard J. Antone, 12284 Adine Ct., Glen Ellen, Calif. 95442
[21] Appl. No.: 931,136
[22] Filed: Aug. 17, 1992
[51] Int. Cl.⁵ .................. G01G 21/22; G01G 23/18; A61B 5/103
[52] U.S. Cl. ..................... 177/253; 177/45; 177/262; 128/774
[58] Field of Search ............. 177/127, 200, 253, 262; 128/774

[56] References Cited
U.S. PATENT DOCUMENTS

| | | |
|---|---|---|
| 2,325,490 | 7/1943 | Elftman ............................ 88/74 |
| 2,653,475 | 9/1953 | Kraus ............................. 177/200 |
| 3,630,299 | 12/1971 | Albagli . |
| 3,774,704 | 11/1973 | Purcell . |
| 4,363,368 | 12/1982 | Paddon et al. . |
| 4,711,313 | 12/1987 | Iida et al. ........................ 177/127 |

FOREIGN PATENT DOCUMENTS 804466  1/1969  Canada ................................ 265/1

Primary Examiner—George H. Miller, Jr.
Attorney, Agent, or Firm—Limbach & Limbach

[57] ABSTRACT

A partial weight-bearing scale including a planar weighing surface and a fixed load supporting platform to one side of the weighing surface. The combination enables a user to stand on the support platform with one foot while applying measured pressure to the scale with the other foot. A visual display is provided to indicate the amount of pressure applied to the scale.

9 Claims, 1 Drawing Sheet

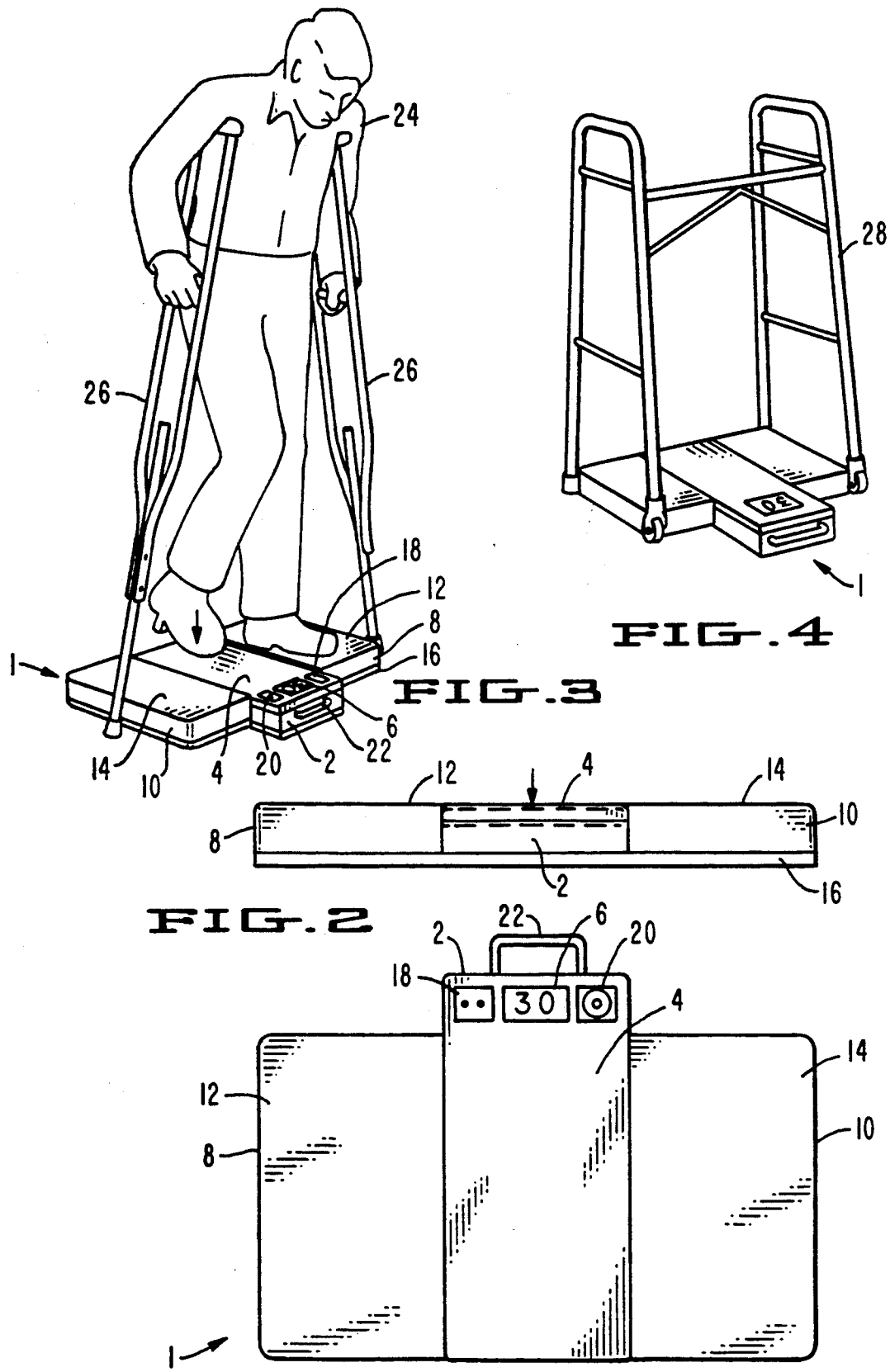

PARTIAL WEIGHT BEARING SCALE

BACKGROUND OF THE INVENTION

1. Field of the Invention

This invention relates to medical care devices, and in particular to the field of physical therapy for accurate measurement of the partial weight placed on the foot, ankle, or leg.

2. Background of the Invention

Hospitals, convalescent homes, and even patient's homes are used for patient rehabilitation after medical operations and procedures. Patients that have had recent medical treatment involving a leg, hip, or foot need to be instructed on how much weight they can safely place on their leg while standing during their recuperation. The danger is that the patient is susceptible to prolonging the recovery period or re-injuring the affected leg, hip or foot if too much weight is placed on it. Usually, the medical doctor will specify what weight can be applied to the recuperating limb without risk of further injury. Many times, that information is passed on to a physical therapist, who is then responsible for properly supervising the patient's recovery. Part of that responsibility involves instructing the patient on how to avoid placing excessive weight on the affected limb.

The inherent danger of injury or re-injury lies in the fact that patients normally do not appreciate just how much pressure they apply to a leg simply by resting it on the ground, or applying what they think is just "a little" weight. Doctors usually instruct their patients to avoid applying more weight to the leg than a specified safe weight. When that specified weight is low, there is a high danger that the patient will put excessive weight on their leg without realizing it. This increases the risk of reinjuring the limb. It is therefore necessary for the medical worker to use a weighing scale to help patients teach themselves what the maximum safe weight "feels" like. The common method used today by health care workers is to instruct patients to step onto a weighing scale with their injured limb and apply weight on it until the maximum amount of allowable pressure is applied on the weighing scale readout.

For patients to effectively gauge the "feel" of the maximum safe weight that can be placed on their injured leg, they must step with their injured leg onto a weighing surface level with the adjacent surface that supports their other foot. Using a conventional weighing scale does not serve this purpose. Weighing scales have a significant thickness to them. Therefore, when a patient places his or her injured leg on the scale, the patient is really stepping up onto a higher surface. This process, therefore, gives the patient the "feel" of the desired weight when stepping up on a higher surface. It does not give the patient the "feel" of the desired weight when resting his or her foot on level ground. Fashioning a temporary adjacent step or support platform of equal height next to the weighing scale does not fully solve the problem because medical workers need a complete scale unit that they can take with them when they go from patient to patient. These workers travel from room to room or to the patient's home. This requires to bring the scale with them. There is a need for a portable scale that measures the weight applied by a patient onto his foot or leg without the patient having to step up to the weighing surface, and without a need for the medical worker to fashion a temporary step of near equal height every time he wants partial weight measured.

Another problem is that when a patient first uses a scale to measure partial weight, there is a tendency for the patient to initially step too hard on their leg and injure themselves. Reactions to weighing scale displays may not be fast enough. There is a need to give the patients quick stimulus to enable them to quickly remove excessive pressure when applied while using the partial weight bearing scale.

SUMMARY OF THE INVENTION

These problems have been overcome by the present invention, which combines a weighing scale and an attached support platform. The present invention provides at least one planar support platform for the patient to stand on that is attached to a weighing scale which also has a planar surface. The two are attached such that both their surfaces are co-planar, and the weighing scale only measures pressure applied to its surface, excluding any weight applied to the support platform. The weight is then visually displayed.

The advantage of this invention over the prior art is that it provides patients with tool that allows them to develop the "feel" of applying the maximum safe pressure allowed that is specified by their doctor while standing on a level surface. The device of the invention is also portable so that the medical worker can easily move the partial weight bearing scale from patient location to patient location.

Another aspect of this invention is that it can incorporate a means for entering a preset weight value such that an audible alarm sounds when the weight applied exceeds the preset weight value. This safety measure ensures that if patients initially apply too much pressure, they can quickly be alerted to remove that pressure to avoid injuring themselves. Presently, if the patient does not react fast enough to the scale display, which usually involves some delay factor, then injury is more likely.

BRIEF DESCRIPTION OF THE DRAWINGS.

FIG. 1 is a plan view of the partial weight bearing scale of the present invention.

FIG. 2 is a side view of FIG. 1 looking directly at the top side that contains the handle.

FIG. 3 is a perspective view diagrammatically showing a manner in which the weighing scale in FIG. 1 can be used by a patient utilizing crutches.

FIG. 4 is a perspective view diagrammatically showing a manner in which the weighing scale in FIG. 1 can be used by a patient utilizing a walker, which fits around the scale.

DETAILED DESCRIPTION OF THE INVENTION

Referring to FIGS. 1 to 4, there is shown the partial weight bearing scale, designated in it's entirety by the number 1. The partial weight bearing scale 1 comprises a weighing scale 2 having a planar weighing surface 4 and a visual display 6, which displays the weight applied to the weighing scale planar surface 4. Support platforms 8 and 10, which have planar surfaces 12 and 14, are attached on each side of the weighing scale 2 such that the support platform planar surfaces 12 and 14 are co-planar with the weighing scale planar surface 4. The attachment can be achieved by a set of screws holding the support platforms 8 and 10 tightly against the weighing scale 2, or by a set of screws that hold the support platforms 8 and 10, and the weighing scale 2, tightly to a solid support board 16, which provides common support to the support platforms 8 and 10 and the weighing scale 2. Support platforms 8 and 10 are attached such that the weighing scale 2 only measures weight applied to the weighing scale surface 4, excluding any weight applied to the support platforms surfaces 12 and 14. An alternate embodiment could provide only a single support platform 8 or 10 on just one side of the weighing scale 2.

The preferred embodiment can include a means for entering a preset weight value through controls 18. If the patient applies weight onto the weighing scale surface 4 that exceeds the preset weight value, an audible alarm sounds from speaker 20 that warns the patient to quickly remove the weight to avoid injury.

The partial weight bearing scale is relatively light for easy transportation. A handle 22 is affixed to the top of the weighing scale 2 to enable the medical care worker or the patient to easily transport the partial weight bearing scale with a single hand, much like a suitcase.

The partial weight bearing scale has total dimensions that enable a person 24 to support themselves while utilizing crutches 26 or a walker 28.

While a preferred embodiment of the invention has been illustrated and described, it should be understood that the invention is not limited to the specifics of this embodiment; but rather is defined by the accompanying claims.

What is claimed is:

1. A partial weight bearing scale that allows a patient to measure the weight placed on a single foot or leg while providing a coplanar support platform for the patient's other foot, comprising:
   (a) a scale having a planar weighing surface;
   (b) at least one support platform having a planar surface;
   (c) means for mounting said support platform to said weighing scale such that the planar surfaces of the scale and platform are co-planar with each other wherein said weighing scale measures weight applied to said weighing scale surface excluding any weight applied to said support platform;
   (d) means for visually displaying weight applied to said weighing surface;
   (e) means for entering a preset weight value into the scale; and,
   (f) an audible alarm that sounds when weight applied to said scale weighing surface exceeds said preset weight value.

2. A partial weight bearing scale as recited in claim 1, wherein the weighing scale and support platform together having total dimensions enabling crutches or a walker to fit around them so that a patient can use said crutches or walker while using said partial weight bearing scale.

3. A partial weight bearing scale as recited in claim 1, further comprising a handle operatively associated with said scale to enable said scale and platform to be lifted as a unit.

4. A method of measuring the partial weight placed upon a patient's single foot or leg while providing a co-planar support platform for the patient's other foot, comprising:
   (a) attaching a planar support platform to a weighing scale having a planar weighing surface such that the weighing surface and support platform are co-planar;
   (b) mounting said weighing scale to said support platform such that said weighing scale only measures pressure applied to said weighing surface excluding any weight applied to sid support platform;
   (c) entering a preset weight value into the scale;
   (d) sounding an alarm when the weight applied to said weighing surface exceeds said preset weight value; and
   (e) displaying visually the weight value applied to said weighing scale.

5. The method of measuring partial weight as recited in claim 4, further comprising: attaching a handle to said weighing scale to enable the scale and platform to be lifted as a unit.

6. A partial weight bearing scale that allows a patient to measure the weight placed on a single foot or leg while providing a coplanar support platform for the patient, comprising:
   (a) weighting means having a planar weighing surface;
   (b) support means for supporting a standing patient, said support means having a planar surface operatively associated with said weighting means such that the weighing surface and the planar surface of the support means are co-planar with each other;
   means for mounting said support means to said weighing means wherein said weighing means only measures weight applied to said weighing surface, excluding any weight applied to the planar surface of said support means;
   (d) means for entering a preset weight value in the weighing means; and,
   (e) means for sounding an alarm when weight applied to the weighing surface of said weighing means exceeds said preset weight value.

7. A partial weight bearing scale as recited in claim 6, further comprising: a handle means to enable said weighing and support means to be lifted as a unit.

8. A partial weight bearing scale that allows a patient to measure the weight placed on a single foot or leg while providing a co-planar support platform for the patient's other foot, comprising:
   (a) a scale having a planar weighing surface;
   (b) support platform means providing planar support surfaces on opposite sides of the weighing surface;
   (c) means for mounting said support platform means to said weighing scale to secure the platform means to the scale with the planar surfaces of the scale and platform means co-planar with each other wherein said weighing scale measures weight applied to said weighing scale surface excluding any weight applied to said support platform means; and,
   (d) means for visually displaying weight applied to said weighing surface.

9. A partial weight bearing scale that allows a patient to measure the weight placed on a single foot or leg while providing a co-planar support platform for the patient's other foot, comprising:
   (a) a scale having a planar weighing surface;
   (b) support platform means providing a fixed non-weight measuring planar support surface to one side of the weighing surface;
   (c) means mounting the support platform means to the weighing scale to secure the platform means to the scale with the planar surfaces of the scale and platform means co-planar with each other wherein said weighing scale measures weight applied to said weighing scale surface excluding any weight applied to said support platform means; and,
   (d) means for visually displaying weight applied to said weighing surface.

* * * * *